United States Patent
Mode et al.

(10) Patent No.: US 6,182,503 B1
(45) Date of Patent: Feb. 6, 2001

(54) ON-LINE RHEOLOGICAL MEASUREMENT FOR PROCESS CONTROL

(75) Inventors: Paul G. Mode, Westfield; Ronald F. Garritano, Flemington, both of NJ (US)

(73) Assignee: Rheometric Scientific, Inc., Piscataway, NJ (US)

( * ) Notice: Under 35 U.S.C. 154(b), the term of this patent shall be extended for 0 days.

(21) Appl. No.: 09/346,255

(22) Filed: Jul. 1, 1999

(51) Int. Cl.$^7$ .................................................. G01N 11/08
(52) U.S. Cl. ................. 73/54.04; 73/863.61; 73/864.34; 422/93; 137/110; 137/115.03
(58) Field of Search .............................. 73/53.01, 54.04, 73/54.07, 54.11, 23.42, 61.56, 863.61, 864.34; 422/70, 89, 93; 137/9, 92, 110, 115.03, 625.3, 629

(56) References Cited

U.S. PATENT DOCUMENTS

| | | | |
|---|---|---|---|
| 2,042,860 | * 6/1936 | Peabody et al. | 137/78 |
| 2,095,282 | * 10/1937 | Payne | 265/11 |
| 3,116,630 | * 1/1964 | Piros | 73/55 |
| 3,137,161 | * 6/1964 | Lewis et al. | 73/55 |
| 3,977,235 | * 8/1976 | Jopham | 73/54 |
| 4,213,747 | * 7/1980 | Friedrich | 425/144 |
| 4,583,395 | * 4/1986 | Anantaraman | 73/55 |
| 4,680,957 | * 7/1987 | Dodd | 73/55 |
| 4,750,351 | * 6/1988 | Ball | 73/55 |
| 4,817,416 | 4/1989 | Blanch et al. | 73/55 |
| 5,172,585 | 12/1992 | Gleissle | 73/54.04 |
| 5,347,852 | 9/1994 | Mode | 73/54.04 |
| 5,633,042 | * 5/1997 | Nakamura et al. | 427/386 |
| 5,637,790 | * 6/1997 | De Corral | 73/54.06 |

* cited by examiner

Primary Examiner—Hezron Williams
Assistant Examiner—David Wiggins
(74) Attorney, Agent, or Firm—Arthur Jacob

(57) ABSTRACT

On-line rheological measurements are made on a process flowing material, such as a polymer melt, utilizing a rheometer of the type in which an inlet pump delivers a relatively large volumetric flow of diverted process material from a process main stream to an inlet site located in very close proximity to the entrance of a capillary passage, and a metering pump draws a smaller portion of the volumetric flow of the diverted material from the inlet site through the capillary passage for return to the process main stream. The viscosity of the diverted material is measured as a function of the rate of flow of the material through the capillary passage and the pressure drop between spaced apart locations along the capillary passage. A parallel flow passage has a volumetric flow capacity considerably greater than the volumetric flow capacity of the capillary passage, an inlet placed at the inlet site, in very close proximity with the entrance of the capillary passage, and an outlet placed downstream of the metering pump. A parallel flow pump in the parallel flow passage moves the balance of the volumetric flow of diverted material from the inlet site for return to the process main stream to assure a continuous supply of fresh diverted material at the entrance to the capillary passage.

10 Claims, 1 Drawing Sheet

ON-LINE RHEOLOGICAL MEASUREMENT FOR PROCESS CONTROL

Figure 1:
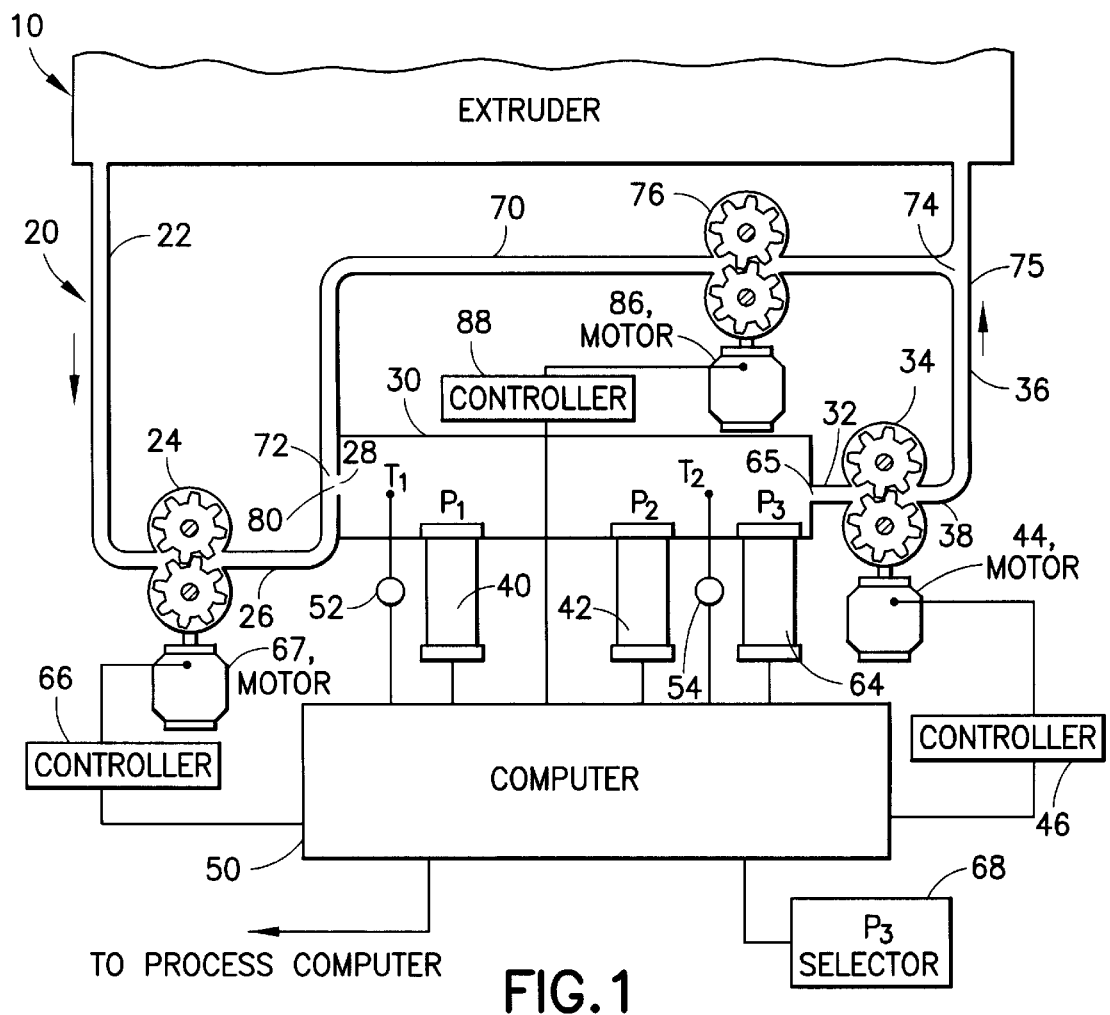

The present invention relates generally to the measurement of rheological characteristics of flowing materials and pertains, more specifically, to the on-line measurement of such characteristics as the viscosity of flowing materials, such as polymer melts, for purposes of control of manufacturing processes involving flowing materials, such as molten plastics.

Rheological testing equipment has been available for a very long time in conducting laboratory measurements of certain important characteristics of flowing materials, such as polymer melts, used in various manufacturing processes. Thus, properties such as viscosity and melt flow index of polymer melts are being measured in the laboratory with increasing accuracy. More recently, efforts have been directed toward the measurement of these characteristics on-line, during the manufacturing process itself, in order to provide constant, closer control over the quality of the material utilized in the process. On-line measurement requires equipment which not only is relatively easy to use and maintain, but which is responsive, and which avoids disturbing the manufacturing process being monitored.

Among the more successful on-line rheometers available currently are capillary rheometers which divert a portion of a polymer melt from the main stream of molten plastic, conduct measurements on the diverted melt, and then either discard the diverted melt or return the diverted melt to the process main stream. In U.S. Pat. No. 4,817,416, the disclosure of which is incorporated herein by reference thereto, there is disclosed an on-line capillary rheometer and techniques for conducting on-line measurements of the type described above. In U.S. Pat. No. 5,347,852, the disclosure of which is incorporated herein by reference thereto, the capability of such on-line rheometers is extended to enable effective use in connection with the control of processes where measurements must be conducted quickly and response time must be held to a minimum, such as processes in which polymers are blended, alloyed or reacted.

The present invention accomplishes still further reductions in response time while increasing the accuracy and effectiveness of Theological measurements conducted on-line. As such, the present invention attains several objects and advantages, some of which are summarized as follows: Enables truly on-line measurements for attaining quicker response and more accurate control of manufacturing processes involving flowing materials, such as polymer melts; allows on-line measurements to be made in a flowing material, such as a polymer melt, diverted from the process main stream with decreased residence time of the diverted material in the measuring apparatus, increased accuracy and quicker response; permits the conduct of on-line measurements with a minimal intrusion into the process being monitored; permits increased versatility in the nature and extent of the information derived from on-line measurements of flowing materials, such as polymer melts, as well as increased accuracy in the information itself; enables ease of installation and use in connection with current manufacturing equipment and techniques; allows ready adaptation for use in connection with a wide variety of materials and operating conditions; enables the maintenance of a continuous flow of material diverted from the process main stream for assuring a supply of fresh material to a rheometer for regular accurate Theological measurements; delivers material to a rheometer for on-line measurements, the material being delivered continuously and at a stabilized temperature for increased accuracy of measurement; allows continuous measurements to be accomplished by an on-line rheometer at selected different volumetric flow rates through the rheometer, while maintaining an essentially constant flow rate in the material diverted from the process main stream for accomplishing accuracy over a range of measurements; and provides a simple and rugged construction for economical manufacture and reliable long-term service.

The above objects and advantages, as well as further objects and advantages, are attained by the present invention, which may be described briefly as apparatus for conducting on-line rheological measurements in a process flowing material carried in a process main stream so as to provide process control information based upon the viscosity of the process flowing material, utilizing a rheometer in which diverted material from a first conduit communicating with the process main stream is delivered downstream to an entrance of a capillary passage having a predetermined volumetric flow capacity, and passes from an exit of the capillary passage to a second conduit, while measuring means measures the viscosity of the diverted material in the capillary passage, the apparatus comprising: an inlet site located in close proximity to the entrance of the capillary passage; an inlet pump having an entrance communicating with the first conduit, and an exit communicating with the inlet site for delivering a volumetric flow of diverted material to the inlet site; a metering pump having an entrance communicating with the exit of the capillary passage, and an exit communicating with the second conduit for drawing a portion of the volumetric flow of diverted material from the inlet site through the capillary passage; a parallel flow passage having an inlet located at the inlet site, between the exit of the inlet pump and the entrance of the capillary passage, in close proximity to the entrance of the capillary passage, and an outlet communicating with the second conduit at a location downstream of the exit of the metering pump; and a parallel passage pump for moving a balance of the volumetric flow of the diverted material from the inlet site through the parallel flow passage to the second conduit so as to assure that a continuous supply of fresh diverted material is available at the inlet site, in close proximity to the entrance of the capillary passage.

Further, the invention includes a method for conducting on-line rheological measurements in a process flowing material carried in a process main stream so as to provide process control information based upon the viscosity of the process flowing material, utilizing a rheometer in which diverted material from a first conduit communicating with the process main stream is delivered downstream to an entrance of a capillary passage having a predetermined volumetric flow capacity, and passes from an exit of the capillary passage to a second conduit, while measuring means measures the viscosity of the diverted material in the capillary passage, the method comprising: providing a volumetric flow of diverted material at an inlet site located in close proximity to the entrance of the capillary passage; drawing a portion of the volumetric flow of diverted material from the inlet site through the capillary passage; and moving a balance of the volumetric flow of diverted material from the inlet site through a parallel passage to assure a continuous supply of fresh diverted material at the inlet site, in close proximity to the entrance of the capillary passage.

Figure 2:
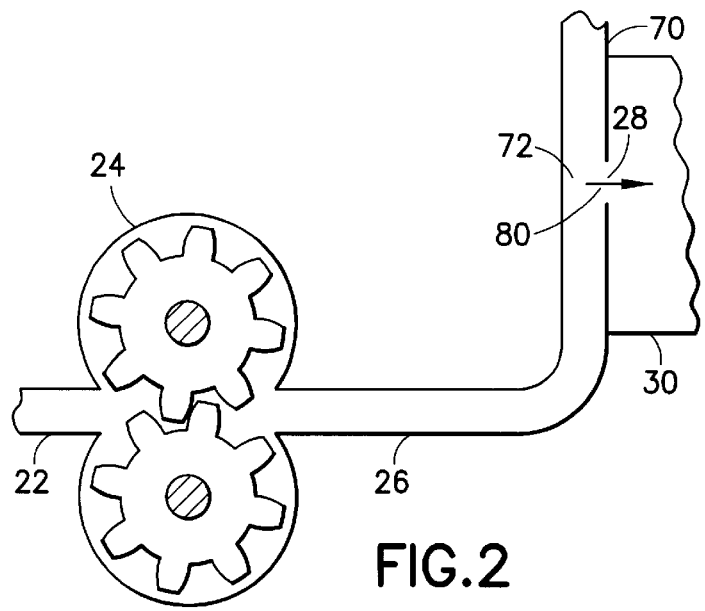

The invention will be understood more fully, while still further objects and advantages will become apparent, in the following detailed description of preferred embodiments of the invention illustrated in the accompanying drawing, in which:

FIG. 1 is a schematic diagram of an on-line system employing the improvement of the present invention; and FIG. 2 is an enlarged fragmentary view of a portion of FIG. 1.

Referring now to the drawing, and especially to FIG. 1 thereof, a plasticating extruder is shown schematically at 10. Extruder 10 is in use, generating melted polymer for the continuous manufacture of plastic material, such as plastic pellets. In order to assure that the quality of the extrudate meets the requirements of the manufacturing process, a control system is utilized in connection with the operation of the extruder 10 to monitor certain characteristics of the polymer melt and to operate the extruder in the manner necessary to attain the desired quality in the extrudate. An on-line rheometer 20, constructed in accordance with the present invention, is a part of that control system.

A portion of the flowing material in the extruder 10, in the form of a polymer melt, is diverted from the process main stream in the extruder 20 through an inlet conduit 22 and is advanced by an inlet pump 24 through an entrance conduit 26 to an entrance 28 of a capillary passage 30 of selected configuration and dimensions, providing the capillary passage 30 with a predetermined volumetric flow capacity. The diverted material, in the form of the polymer melt, traverses the capillary passage 30 and then leaves the capillary passage 30 via an exit conduit 32. A metering pump 34 draws the diverted polymer melt through the capillary passage 30 and then advances the diverted polymer melt through an outlet conduit 36 which is connected to outlet 38 of the metering pump 34 and preferably communicates with the extruder 10 so that the outlet conduit 36 is a return conduit and the diverted polymer melt is returned to the process main stream of polymer melt in the extruder 10. A first pressure-responsive transducer 40 is placed at a location adjacent the entrance 28 and provides information indicative of the pressure $P_1$ in the polymer melt at that location in the capillary passage 30. A second pressure-responsive transducer 42 is placed at a second location spaced downstream from the first location and provides information indicative of the pressure $P_2$ at the second location in the capillary passage 30. The rate of flow of the polymer melt in the capillary passage 30 is governed by the speed of the metering pump 34 and that speed is determined by the speed of the motor 44 which drives the metering pump 34. The speed of motor 44 is controlled by a controller 46 which itself is connected to a computer 50. Temperature sensors 52 and 54 provide information to computer 50 indicative of the temperature ($T_1$ and $T_2$) of the polymer melt adjacent each of the locations of the pressure-responsive transducers 40 and 42.

The pressure drop $P_1-P_2$ is maintained constant by controlling the speed of the metering pump 34. The speed of the metering pump 34 then provides a measure of the rate of flow of the polymer melt traversing the capillary passage 30, which rate of flow is an indication of the viscosity of the polymer melt. Since the speed of the metering pump 34 is known with precision, the viscosity is determined with a high degree of accuracy. Since the temperature dependence of polymer materials at constant stress is well known, the maintenance of a constant stress on the polymer melt in the capillary passage 30, that is, the maintenance of a constant pressure drop $P_1-P_2$, enables the temperature information, as determined by $T_1$ and $T_2$ (preferably by averaging $T_1$ and $T_2$), to be utilized to relate the measurements to a known standard so that it is not necessary to control the temperature of the diverted polymer melt, but merely to measure the temperature and then correct the measured viscosity information, in accordance with the measured temperature, to derive the desired control information. In this manner, viscosity measurements are enabled independent of the temperature of the diverted polymer melt. The information pertaining to pressure drop ($P_1-P_2$), rate of flow and temperature ($T_1$ and $T_2$) is directed to computer 50. Computer 50 then provides control information to a process computer which may be used in connection with the control of the operation of the extruder 10.

In order to maintain accuracy in the determination of viscosity, utilizing the above scheme, it is necessary to assure that the pressure drop ($P_1-P_2$) is solely a result of the traverse of the capillary passage 30 by the polymer melt, and that the measured pressures are not affected by any irregularities in the operation of the various components of the rheometer 20. A third pressure-responsive transducer 64 is located adjacent exit 65 from the capillary passage 30 and provides information indicative of the pressure $P_3$ at the exit. The information provided by the third pressure-responsive transducer 64 is utilized by the computer 50 to operate a controller 66 so that a motor 67 actuates the inlet pump 24 at the speed necessary to maintain the pressure $P_3$ constant. By maintaining the exit pressure $P_3$ constant, the pressure drop $P_1-P_2$ is related solely to the characteristics of the polymer melt traversing the capillary passage 30 and does not include any effects introduced by inaccuracies in the mechanical components of the rheometer 20. Hence, the information provided by computer 50 is related solely to the characteristics of the polymer melt for accurate control of the process being carried out in the extruder. In response to selected input into the computer 50, by means of a selector 68, the exit pressure $P_3$ can be changed to any selected constant pressure enabling the measurement of the viscosity of the polymer melt at different pressures, thereby enabling an evaluation of the response of viscosity to pressure. These measurements provide additional information enabling enhanced control of the quality of the extrudate produced by the extruder 10.

In order to reduce residence time and decrease response time, thereby enabling even more truly on-line operation, a parallel flow passage 70 has an inlet 72 placed between the inlet pump 24 and the entrance 28 to the capillary passage 30, in close juxtaposition with the entrance 28, and an outlet 74 communicating with the outlet or return conduit 36, at a location 75 downstream of the outlet 38 of the metering pump 34. A parallel passage pump 76 is placed in the parallel flow passage 70 for controlling the flow of diverted melt through the parallel flow passage 70. The volumetric flow capacity of the parallel flow passage 70 preferably is considerably greater than the volumetric flow capacity of the capillary passage 30, as is the predetermined volumetric flow capacity of the inlet conduit 22 and the predetermined volumetric flow capacity of the outlet conduit 36. In some instances, the volumetric capacity of the parallel flow passage 70 is up to several hundred times the volumetric flow capacity of the capillary passage 30. Operation of the parallel passage pump 76, in concert with the inlet pump 24, delivers a relatively high volumetric flow of fresh melt very quickly from the extruder 10 to an inlet site 80 located in very close proximity to, and preferably essentially contiguous with, the entrance 28 of the capillary passage 30, as best seen in FIG. 2. Operation of the metering pump 34 then draws a portion of the volumetric flow of fresh melt presented at the inlet site 80 through the capillary passage 30 for accomplishing the desired measurement. The portion of the volumetric flow of fresh melt drawn through the capillary passage 30 very often is small as compared to the considerably greater volumetric flow of fresh melt delivered to the inlet site 80, and the balance of the much larger volumetric flow of diverted melt is moved by the parallel passage pump 76 through the parallel passage 70 to the outlet or return conduit 36. In this manner, a fresh supply of diverted melt is moved quickly from the extruder 10 to the capillary passage 30 at a rate of flow which is not limited to the volumetric flow capacity of the capillary passage 30, and a supply of fresh diverted melt is made available for measurement more rapidly for quicker response, unrestricted by the flow capacity of the capillary passage 30. The very close proximity of the inlet site 80 to the entrance 28 of the capillary passage 30, and the very close proximity of the inlet 72 of the parallel passage 70 to the entrance 28 of the capillary passage 30 minimizes any dead volume of diverted melt at the inlet site 80, assuring that an appropriate volumetric flow of fresh melt always is available at the entrance 28 of the capillary passage 30 to be drawn through the capillary passage 30 by the metering pump 34 for conducting the desired measurements. Parallel passage pump 76 is driven by motor 86, under the control of a controller 88 which, in turn, is controlled by computer 50.

With fresh melt being continuously available at the entrance 28 of the capillary passage 30, measurements can be conducted continuously, without any interruption due to any necessity for purging the system to assure the presence of fresh melt. Moreover, the flow rate of diverted melt through the capillary passage 30 may be varied by varying the speed of the metering pump 34, while the overall flow rate through the rheometer 20 is maintained constant, thereby enabling measurements to be conducted at selected different flow rates for increased versatility of measurement. Thus, measurements can be carried out over sweeps of different volumetric flow rates for added versatility and accuracy. Further, the overall flow rate of diverted melt through the rheometer 20 is the sum of the volumetric flow rate through the metering pump 34 and flow rate through the parallel passage pump 76. The overall flow rate is maintained constant by control of the speed of the parallel passage pump 76 independent of the speed of the metering pump 34, through controllers 88 and 46, while the pressure drop $P_1-P_2$ is measured. The maintenance of a constant overall flow rate through the rheometer 20 attains stabilization of the temperature of the diverted melt in the rheometer 20 for greater accuracy of measurement.

It will be seen that the above-described apparatus and procedure attains the several objects and advantages summarized above, namely: Enables truly on-line measurements for attaining quicker response and more accurate control of manufacturing processes involving flowing materials, such as polymer melts; allows on-line measurements to be made in a flowing material, such as a polymer melt, diverted from the process main stream with decreased residence time of the diverted material in the measuring apparatus, increased accuracy and quicker response; permits the conduct of on-line measurements with a minimal intrusion into the process being monitored; permits increased versatility in the nature and extent of the information derived from on-line measurements of flowing materials, such as polymer melts, as well as increased accuracy in the information itself; enables ease of installation and use in connection with current manufacturing equipment and techniques; allows ready adaptation for use in connection with a wide variety of materials and operating conditions; enables the maintenance of a continuous flow of material diverted from the process main stream for assuring a supply of fresh material to a rheometer for regular accurate rheological measurements; delivers material to a rheometer for on-line measurements, the material being delivered continuously and at a stabilized temperature for increased accuracy of measurement; allows continuous measurements to be accomplished by an on-line rheometer at selected different volumetric flow rates through the rheometer, while maintaining an essentially constant flow rate in the material diverted from the process main stream for accomplishing accuracy over a range of measurements; and provides a simple and rugged construction for economical manufacture and reliable long-term service.

It is to be understood that the above detailed description of embodiments of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. Apparatus for conducting on-line rheological measurements in a process flowing material carried in a process main stream so as to provide process control information based upon the viscosity of the process flowing material, utilizing a rheometer in which diverted material from a first conduit communicating with the process main stream is delivered downstream to an entrance of a capillary passage having a predetermined volumetric flow capacity, and passes from an exit of the capillary passage to a second conduit, while measuring means measures the viscosity of the diverted material in the capillary passage, the apparatus comprising:

an inlet site located in close proximity to the entrance of the capillary passage;

an inlet pump having an entrance communicating with the first conduit, and an exit communicating with the inlet site for delivering a volumetric flow of diverted material to the inlet site;

a metering pump having an entrance communicating with the exit of the capillary passage, and an exit communicating with the second conduit for drawing a portion of the volumetric flow of diverted material from the inlet site through the capillary passage;

a parallel flow passage having an inlet located at the inlet site, between the exit of the inlet pump and the entrance of the capillary passage, in close proximity to the entrance of the capillary passage, and an outlet communicating with the second conduit at a location downstream of the exit of the metering pump; and a parallel passage pump for moving a balance of the volumetric flow of the diverted material from the inlet site through the parallel flow passage to the second conduit so as to assure that a continuous supply of fresh diverted material is available at the inlet site, in close proximity to the entrance of the capillary passage.

2. The invention of claim 1 wherein the inlet site is essentially contiguous with the entrance of the capillary passage.

3. The invention of claim 1 wherein the parallel flow passage has a volumetric flow capacity considerably greater than the volumetric flow capacity of the capillary passage.

4. The invention of claim 3 wherein the inlet site is essentially contiguous with the entrance of the capillary passage.

5. The invention of claim 1 wherein the second conduit communicates with the process main stream for returning the diverted material to the process main stream.

6. A method for conducting on-line rheological measurements in a process flowing material carried in a process main stream so as to provide process control information based upon the viscosity of the process flowing material, utilizing a rheometer in which diverted material from a first conduit communicating with the process main stream is delivered downstream to an entrance of a capillary passage having a predetermined volumetric flow capacity, and passes from an exit of the capillary passage to a second conduit, while measuring means measures the viscosity of the diverted material in the capillary passage, the method comprising:

provi ding a volumetric flow of diverted material at an inlet site located in close proximity to the entrance of the capillary passage;

drawing a portion of the volumetric flow of diverted material from the inlet site through the capillary passage; and moving a balance of the volumetric flow of diverted material from the inlet site through a parallel passage to assure a continuous supply of fresh diverted material at the inlet site, in close proximity to the entrance of the capillary passage.

7. The invention of claim 6 wherein the volumetric flow of material provided to the inlet site is considerably greater than the volumetric flow capacity of the capillary passage.

8. The invention of claim 6 wherein the inlet site is located essentially contiguous with the entrance of the capillary passage so that the volumetric flow of diverted material is located essentially contiguous with the entrance of the capillary passage.

9. The invention of claim 6 including returning the portion of the volumetric flow of diverted material to the process main stream.

10. The invention of claim 6 including returning the balance of the volumetric flow of diverted material to the process main stream.

* * * * *